United States Patent [19]

Wang et al.

[11] Patent Number: 5,972,934
[45] Date of Patent: Oct. 26, 1999

[54] STABILIZED NITHIAZINE COMPOSITIONS

[75] Inventors: I-Hsiung Wang; Kim W. Yang, both of Dallas, Tex.; James M. Richmond, Naperville, Ill.

[73] Assignee: Novartis AG, Basel, Switzerland

[21] Appl. No.: 08/681,754

[22] Filed: Jul. 29, 1996

[51] Int. Cl.[6] .................................................. A61K 31/54
[52] U.S. Cl. ......................................................... 514/226.8
[58] Field of Search .......................................... 514/226.8

[56] References Cited

U.S. PATENT DOCUMENTS

| | | | |
|---|---|---|---|
| 3,933,809 | 1/1976 | Powell | 260/243 R |
| 3,985,736 | 10/1976 | Powell et al. | 260/243 R |
| 3,993,648 | 11/1976 | Powell | 260/243 R |
| 4,052,388 | 10/1977 | Powell | 260/243 R |
| 4,065,560 | 12/1977 | Powell | 424/246 |
| 4,225,603 | 9/1980 | Tieman | 424/246 |
| 4,486,427 | 12/1984 | Estreicher et al. | 424/246 |
| 4,529,726 | 7/1985 | Harris | 514/226 |

FOREIGN PATENT DOCUMENTS

| | | | |
|---|---|---|---|
| 57-18604 | 1/1982 | Japan | 514/226.8 |
| 57-18605 | 1/1982 | Japan | 514/226.8 |
| 57-2208 | 1/1982 | Japan | 514/226.8 |
| 59-134703 | 8/1984 | Japan | 514/226.8 |
| 59-204110 | 11/1984 | Japan | 514/226.8 |

*Primary Examiner*—Allen J. Robinson
*Attorney, Agent, or Firm*—Michael P. Morris; John D. Peabody, III

[57] ABSTRACT

Stabilized compositions of nithiazine which are suitable for long term use in an agricultural application. The compositions typically contain nithiazine, a hydroxyalkyl-tert-amine and an antioxidant. Suitable hydroxyalkyl-tert-amines include, for example, triethanolamine, 4-(2-hydroxyethyl) morpholine, N-(2-hydroxyethyl)pyrrolidine, ETHOMEEN S12®, ETHOMEEN C12® and ETHOMEEN T12®. Suitable antioxidants include, for example, TENOX GT-2® (a mixture of 70% tocopherols) and alkyl gallates.

11 Claims, 1 Drawing Sheet

NITHIAZINE (TTNM)

TRIETHANOLAMINE 4-(2-HYDROXYETHYL) MORPHOLINE

R = SAYALKYL (ETHOMEEN S/12)
R = TALLOW (ETHOMEEN T/12)

TENOX GT-2 ANITOXIDANT: 70 PERCENT TOCOPHEROLS

PROPYL GALLATE

STABILIZED NITHIAZINE COMPOSITIONS

BACKGROUND OF THE INVENTION

Nithiazine, 2-nitromethylene-tetrahydro-2H-1,3-thiazine is an active ingredient in a number of insecticidal compositions. It has been described as having activity against rice insects including both moths and flies. However, nithiazine is a relatively unstable compound which will decompose under thermal, sunlight, or moisture conditions.

A number of approaches have been investigated in an effort to stabilize nithiazine formulations. Japan patent JP 57002208 reports the stabilization of nithiazine using α- and β- naphthols or phenols having two to three hydroxy radicals attached to the benzene ring. In Japan patent JP 5718604, nithiazine is stabilized with potassium salts of carboxylic acids or phosphoric acids. Japan patent JP 5718605 describes the stabilization of nithiazine with urea or thiourea. More recently, JP 59134703 described the use of secondary aromatic amines such as N-methylaniline, N-methyltoluidine, diphenylamine and N-phenyl-βnaphthylamine to prevent decomposition of nithiazine.

Despite the above approaches, there exists a need for compositions which provide a long-term stabilization of nithiazine to both thermal and UV conditions. Surprisingly, the present invention provides such compositions.

SUMMARY OF THE INVENTION

The present invention provides stabilized compositions of nithiazine which are suitable for long term use in an agricultural application. The compositions typically comprise nithiazine, a hydroxyethyl-tert-amine and an antioxidant. Suitable hydroxyethyl-tert-amines include, for example, triethanolamine, 4(2-hydroxyethyl)morpholine, N-(2-hydroxyethyl)pyrrolidine and lipophilic amine ethoxylates such as ETHOMEEN C12® ETHOMEEN S120 and ETHOMEEN T12®. Suitable antioxidants include, for example, TENOX GT-2® (a mixture of 70% tocopherols), alkyl gallates, sodium bisulfite and 2,6-di-tert-butyl-4-methylphenol.

DETAILED DESCRIPTION OF THE INVENTION

Abbreviations and Definitions

The following abbreviations are used herein: AcOH, acetic acid; Boc, t-butoxycarbonyl; DME, dimethoxyethane; DMF, dimethylformamide; EtOAc, ethyl acetate; NMP, N-methyl-pyrrolidone; TEA, triethanolamine; TTNM, nithiazine; TFA, trifluoroacetic acid; ETHOMEEN ethanol; ETHOMEEN C12®, N-Cocoalkyl-2,2'-Iminobis-ethanol; ETHOMEEN T12®, N-Tallowalkyl-2,2'-Ininobisethanol; Tenox GT-2® =Tocopherols.

Nithiazine Compositions

The present invention provides stabilized compositions of nithiazine which are suitable for agricultural uses, particularly for the control of insect pests associated with rice production. The nithiazine compositions typically comprise nithiazine (2-nitromethylene-tetrahydro-2H-1,3-thiazine, or TTNM), a thermal stabilizing agent, an antioxidant and inert carriers. In preferred embodiments, the compositions will further comprise a solvatochromic compound.

For use in the present invention, nithiazine can be prepared by any of the methods described in U.S. Pat. Nos. 3,993,648 and 4,065,560. Other materials, including thermal stabilizers, antioxidants, solvatochromic compounds and inert carriers are all commercially available.

While the present invention recites stabilized compositions of nithiazine, the formulations provided herein will find equal application for other derivatives and analogs of 2-nitromethylene-tetrahydro-2H-1,3-thiazine, such as those described in U.S. Pat. Nos. 3,933,809, 3,985,736, 4,225,603, 4,052,388, 4,529,726 and 4,486,427, the disclosures of which are incorporated herein by reference.

The amount of nithiazine in the present compositions will depend on the particular formulation which is being produced (ie., a wettable powder, dust, granules, emulsifiable concentrate, emulsion, suspension concentrate or aerosol). These amounts are discussed in more detail below. Nevertheless, the amount of nithiazine will provide the basis by which appropriate amounts of the stabilizing components are measured.

Figure 1:
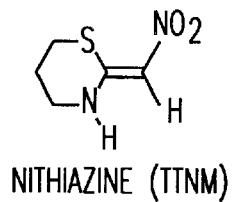
FIG. 1 provides the structures of nithiazine as well as several thermal stabilizers and antioxidants.
Figure 1:
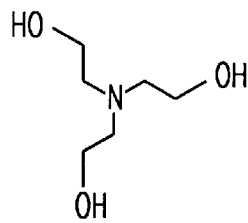
Figure 1:
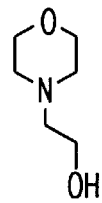
Figure 1:
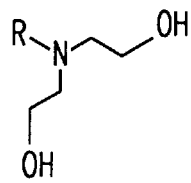
Figure 1:
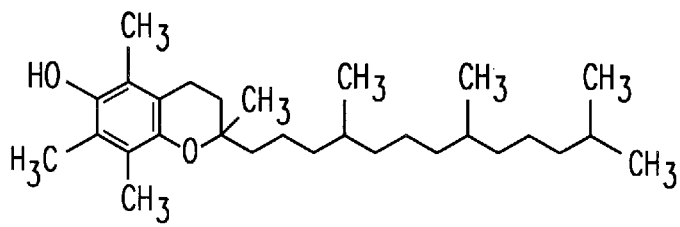
Figure 1:
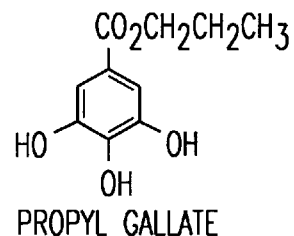

Thermal stabilizing agents which are used in the present composition will typically be a hydroxyalkyl-tert-amine. As used herein, the term "hydroxyalkyl-tert-amine" refers to an amine which is trisubstituted wherein at least one of the three substituents is a hydroxy substituted alkyl group in which the alkyl portion is either straight chain or branched and has from two to twelve carbon atoms. Examples of hydroxyalkyl-tert-amines include triethanolamine, 4-(2-hydroxyethyl)morpholine, N-(2-hydroxyethyl)pyrrolidine, 4-(3-hydroxypropyl)morpholine, N-(3-hydroxypropyl) pyrrolidine, 4-(2-hydroxypropyl)morpholine, N-(2-hydroxypropyl)pyrrolidine and lipophilic amine ethoxylates such as, for example, ETHOMEEN S12®, ETHOMEEN C12®, and ETHOMEEN T12® (see FIG. 1). Preferably, the hydroxyalkyl-tert-amine is hydrophobic. The hydroxyalkyl-tert-amines will preferably be present in an amount which is dependent on the amount of nithiazine which is present. For example, the amount of thermal stabilizing agent will preferably be from about 1.0 to about 200 mole %, relative to the molar amount of nithiazine. More preferably, the amount will be about 5 to about 50 mole %. In the most preferred embodiments, the thermal stabilizing agent will be present in an amount of about 5 to about 10 mole %.

Antioxidants which are useful in the present invention include, for example, alkyl gallates, tocopherols, retinol, butylated hydroxytoluene, butylated hydroxyanisol, stilbene, or combinations thereof. In preferred embodiments the antioxidant is an alkyl gallate, a mixture of tocopherols, or combinations thereof. More preferably, the compositions will contain propyl gallate, TENOX GT-2®, or a combination of the two. As with the thermal stabilizing agents, the amount of antioxidant will typically depend on the amount of nithiazine which is present. As a result, the amount of antioxidant is presented as a mole % relative to nithiazine. The amount of antioxidant present in the compositions will typically be about 1.0 to about 200 mole %, more preferably about 1.0 to about 30 mole %. In the most preferred embodiments, the antioxidant will be present in an amount of about 2.0 to about 10 mole %.

Solvatochromic compounds which are useful in the present compositions include merocyanine dyes and meropolymethine dyes. When used, these compounds will typically be present in the compositions in an amount of from about 0.5 to about 50 weight %, more preferably about 0.5 to about 25 weight %. In the most preferred embodiments, the antioxidant will be present in an amount of about 0.5 to about 10 weight %.

The remainder of the present compositions will typically comprise inert carriers, surface-active agents or both. The term "carrier" as used herein means an inert, horticulturally acceptable material (i.e., non-phytotoxic when applied to plants), that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen; waxes such as beeswax, paraffin wax, and chlorinated mineral waxes; degradable organic solids, such as ground corn cobs and walnut shells; and solid fertilizers, for example superphosphates.

Suitable liquid carriers include solvents for nithiazine and related compounds, as well as liquids in which nithiazine is insoluble or only slightly soluble. Examples of such solvents and liquid carriers, generally, are alcohols, for example, ethyl alcohol or isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified, normally vaporous, gaseous compounds. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products: alkali or alkaline earth metal salts, preferably sodium salts, of sulfuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide. In some embodiments, the thermal stabilizing agent is a lipophilic amine ethoxylate, which can also serve as a surface-active agent when present in sufficient quantity.

Using the components above, and methods well-known to those of skill in the art, the compositions of the invention may for example be formulated as wettable powders, dusts, granules, solutions, emulsifiable concentrates, emulsions, suspension concentrates and aerosols.

Wettable powders usually contain 25, 50 or 75% by weight of active ingredient and usually contain in addition to solid inert carrier, 3–10% by weight of a dispersing agent, the appropriate amount of thermal stabilizing agents and antioxidants, and other additives such as penetrants or stickers, when necessary. Dusts are usually formulated as a dust concentrate having a similar composition to that of a wettable powder but without a dispersant, and are diluted in the field with further solid carrier to give a composition usually containing ½–10% by weight of active ingredient. Granules are usually prepared to have a size between 10 and 100 BS mesh (1.676–0.152 mm), and may be manufactured by agglomeration or impregnation techniques. Generally, granules will contain ½–75% by weight of nithiazine and 0–10% by weight of additives such as the stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% weight/volume of active ingredient, 2–20% weight/volume emulsifiers and 0–20% weight/volume of other additives such as the above-noted stabilizers, penetrants and corrosion inhibitors. Suspension concentrates are usually compounded so as to obtain a stable, non-sedimenting flowable product and usually contain 10–75% by weight active ingredient, the above-indicated amounts of thermal stabilizing agents and antioxidants, 0.5–15% by weight of dispersing agents, 0.1–10% by weight of suspending is agents such as protective colloids and thixotropic agents, 0–10% by weight of other additives such as defoamers, corrosion inhibitors, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this invention at the locus to be protected—i.e. the applied dosage—is of the order of 0.01% to 0.5% based on the total weight of the formulation, though under some circumstances the effective concentration will be as little as little as 0.001% or as much as 2%, on the same basis.

The foregoing description and the following examples are offered primarily for illustration and not as limitations. It will be readily apparent to those of ordinary skill in the art that the operating conditions, materials, procedural steps and other parameters of the system described herein may be further modified or substituted in various ways without departing from the spirit and scope of the invention.

EXAMPLES

Materials

Nithiazine was obtained from DuPont (Wilmington, Del., U.S.A). Triethanolamine, 4-(2-hydroxyethyl)morpholine, propyl gallate and methyl gallate were obtained from Aldrich Chemical Co. (Milwaukee, Wis., U.S.A). ETHOMEEN S12®, ETHOMEEN C12® and ETHOMEEN T12® were obtained from Akzo Nobel Chemical Inc. (Chicago, Ill., U.S.A). TENOX GT-2® was obtained from Eastman Chemical Company (Kingsport, Tenn., U.S.A).

General Methods

For the nithiazine stabilization experiments below, the following experimental procedures were followed.

To a flask of ethanol was added an appropriate buffer, tiethanolamine, or a hydroxy-ethyl-tert-amine along with nithiazine and an antioxidant or compound. The mixture was stirred and inert ingredients (i.e. sucrose, pvp 120) were added. After mixing, the resulting composition was applied to glass slides and air dried for two days. The slides were stored in an amber-colored glass jar without desiccant until subjected to thermal or UV conditions for the assay.

Thermal Sensitivity Test

For thermal sensitivity, the glass slides were heated on a hot plate to the indicated temperature (typically 40° C.) for the indicated time. The composition which remains is removed from the slide and analyzed using high performance liquid chromatography (HPLC) to quantify the amount of nithiazine which remains.

UV Sensitivity Test

In a manner similar to the above thermal sensitivity test, glass slides are coated with the indicated composition and subjected to UV irradiation for the period of time noted in the tables. The amount of remaining nithiazine is determined using HPLC analysis.

Example 1

This example illustrates the ability of triethanolamine CIBA) to increase the thermal stability of nithiazine (TTNM).

1.1 Initial Stability Studies

Thermal stability tests were carried out as described in the General Methods section. The percent of TTNM remaining on the slides was measured after 21, 49, 57 and 137 or 157 days. Results are presented in Table 1.

TABLE 1

Thermal Stability of Nithiazine Formulations at 40° C.
Nithiazine 0.006 mole
Data in ( ) represents % nithiazine remaining

| TEA | Initial | 21 days | 49 days | 57 days | 137 days | 157 days |
|---|---|---|---|---|---|---|
| 0 mole | 3.7702 | 1.8803 | 0.7559 (20%) | 0.8429 (22%) | 0.2015 (5.3%) | |
| 0.006 mole | 3.2534 | 2.7886 (86%) | 2.0872 (64%) | 2.0861 (64%) | | 1.3236 (41%) |

1.2 Stability Studies as a Function of TEA/TTNM Mole Ratio

The effect of TEA/TTNM mole ratio on the thermal stability of the composition was evaluated at 40° C. using the test described above. The results are presented in Table 2 as the percent of TTNM remaining on the slides.

TABLE 2

Thermal Stability of Nithiazine Formulations at 40° C.
Nithiazine 0.006 mole

| TEA/nithiazine mole ratio | Initial | 7 days | 14 days | 21 days | 28 days |
|---|---|---|---|---|---|
| 0.50 | 3.4620 | 3.3433 | 3.2969 | 3.3420 | 3.0633 (89%) |
| 1.00 | 3.3332 | 3.3072 | 3.2768 | 3.1667 | 2.9419 (88%) |
| 1.68 | 3.0493 | 3.0423 | 2.9048 | 2.8777 | 2.6753 (88%) |
| 2.54 | 3.8579 | 2.9702 | 2.8576 | 2.7222 | 2.6012 (67%) |

Example 2

This example illustrates the effect of the antioxidant propyl gallate on the thermal and UV stability of a formulation containing triethanolamine (0.0067 mole) and nithiazine (0.0063 mole). The tests were conducted as described above. Thermal stability results are provided in Tables 3 and 4, while UV stability results are provided in Table 5. Data in () represents % nithiazine remaining. The stability tests were conducted as described above.

TABLE 3

Thermal Stability of Nithiazine/TEA/Propyl Gallate Formulations

| Antioxidant | initial | 7 days | 15 days | 45 days | 66 days | 84 days | 114 days |
|---|---|---|---|---|---|---|---|
| Propyl gallate (0.0068 mole) | 3.2369 | 3.0401 (94%) | 3.1970 (99%) | 2.7798 (86%) | 2.4474 (77%) | 2.1008 (65%) | 1.6758 (52%) |
| Propyl gallate (0.0097 mole) | 3.2514 | 2.9243 (90%) | 3.1024 (95%) | (2.7965 (86%) | 2.3373 (72%) | 1.7538 (54%) | 1.2758 (39%) |
| Propyl gallate (0.0126 mole) | 3.2425 | 3.0882 (95%) | 3.1057 (96%) | 2.6677 (83%) | 1.9574 (60%) | 1.3273 (41%) | 0.9439 (29%) |

TABLE 4

Thermal Stability of Nithiazine/TEA/Propyl Gallate Formulations

| Antioxidant | initial | 14 days | 22 days | 51 days | 72 days | 101 days | 120 days |
|---|---|---|---|---|---|---|---|
| Propyl gallate (0.0016 mole) | 3.3225 | 3.4321 (103%) | 3.1849 (96%) | 3.1132 (94%) | 2.9060 (87%) | 2.5565 (74%) | 2.3625 (71%) |

The combination of triethanolamine and antioxidant (e.g. propyl gallate) increases the nithiazine stability relative to those compositions without antioxidant (Table 1 and Table 2).

TABLE 5

UV Stability of Nithiazine/TEA/Propyl Gallate Formulations

| Antioxidant | initial | 20 hr | 28 hr | 44 hr | 51 hr |
|---|---|---|---|---|---|
| Propyl gallate | 3.2369 | 2.7955 (86%) | 2.7005 (83%) | 2.5782 (80%) | 2.4698 (76%) |
| Propyl gallate (0.0098 mole) | 3.2514 | 2.7234 (84%) | 2.6086 (80%) | 2.4782 (76%) | 2.4207 (75%) |
| Propyl gallate (0.0126 mole) | 3.2425 | 2.7180 (84%) | 2.5911 (80%) | 2.4362 (75%) | 2.4482 (76%) |

Example 3

This example provides a comparison of the stabilizers triethanolamine and 4-(2-hydroxyethyl)morpholine and further illustrates the effect of adding a hydrophobic hydroxyethyl-tert-amine (e.g., 4-(2-hydroxyethyl) morpholine or ETHOMEEN) and hydrophobic antioxidants (TENOX). Long term stability is increased as shown in Tables 8, 9 and 11. As a comparison, data is provided for formulations in which the more hydrophobic hydroxyethyl-tert-amines such as 4(2-hydroxyethyl) morpholine and hydrophobic antioxidant such as TENOX GT-2® are used in place of the more hygroscopic triethanolamine (see Tables 6 and 7). As Tables 6–11 illustrate, using hydrophobic tert-amines and antioxidant in combination can provide substantial increases in nithiazine long term stability. All tests were conducted as described above.

TABLE 6

Thermal Stability of Nithiazine/Propyl Gallate/tert-Amine at 40° C.
Nithiazine (0.0063 mole)
Propyl gallate (0.007 mole)

| Stabilizer | Initial | 8 days | 38 days | 60 days | 87 days | 105 days | 141 days |
|---|---|---|---|---|---|---|---|
| 4-(2-hydroxyethyl) morpholine (0.0071 mole) | 3.2097 | 3.2064 (100%) | 2.9923 (93%) | 2.8604 (89%) | 3.0037 (94%) | 2.8321 (88%) | 2.4150 (75%) |
| Triethanolamine (0.007 mole) | 3.6659 | 3.7263 (102%) | 3.5547 (97%) | 3.1445 (86%) | 2.7884 (76%) | 1.3236 (36%) | — |

TABLE 7

UV Stability of Nithiazine/Propyl Gallate/tert-Amine

| Stabilizer | Initial | 6 hr | 23 hr | 30 hr | 46 hr |
|---|---|---|---|---|---|
| 4-(2-hydroxyethyl)-morpholine (0.0071 mole) | 3.2097 | 2.8504 (89%) | 2.4571 (77%) | 2.3573 (73%) | 2.1555 (67%) |
| Triethanolamine (0.007 mole) | 3.6659 | 3.3246 (91%) | 2.9537 (81%) | 2.7930 (76%) | 2.5487 (70%) |

TABLE 8

Thermal Stability of Nithiazine/TEA/TENOX Formulations at 40° C.
Nithiazine (0.006 mole)
TEA (0.006 mole)

| TENOX | Initial | 11 days | 25 days | 33 days | 64 days | 85 days |
|---|---|---|---|---|---|---|
| TENOX (0.0005 mole) | 3.4970 | 3.2013 (92%) | 3.0989 (89%) | 3.1275 (89%) | 2.7890 (80%) | 2.4005 (69%) |

TABLE 8-continued

Thermal Stability of Nithiazine/TEA/TENOX Formulations at 40° C.
Nithiazine (0.006 mole)
TEA (0.006 mole)

| TENOX | Initial | 11 days | 25 days | 33 days | 64 days | 85 days |
|---|---|---|---|---|---|---|
| TENOX (0.006 mole) | 3.3923 | 3.0462 (90%, 30 days) | 2.7482 (81%, 51 days) | 2.6141 (77%, 79 days) | 2.3966 (71%, 99 days) | |

TABLE 9

Thermal Stability of Nithiazine/TEA or
ETHOMEEN S12 ®/TENOX Formulations at 40° C.
Nithiazine 0.0062 mole
Tenox 0.0007 mole

| Stabilizer | Initial | 23 days | 43 days |
|---|---|---|---|
| ETHOMEEN S12 ® (0.0009 mole) | 5.5512 | 5.5379 (99.8%) | 5.1938 (94%) |
| TEA (0.0043 mole) | 5.7157 | 3.7263 (88%) | 4.2602 (75%) |

TABLE 10

UV Stability of Nithiazine/TEA or
ETHOMEEN S12 ®/TENOX Formulations
Nithiazine 0.0062 mole
Tenox 0.0007 mole

| Stabilizer | Initial | 7 hr | 23 hr | 31 hr | 47 hr |
|---|---|---|---|---|---|
| ETHOMEEN S12 ® (0.0009 mole) | 5.5512 | 4.4714 (90%) | 3.3478 (71%) | 3.0381 (66%) | 2.7054 (57%) |
| TEA (0.0043 mole) | 5.7157 | 4.2853 (75%) | 2.2385 (39%) | 1.6550 (29%) | 1.3153 (23%) |

TABLE 11

Thermal Stability of Nithiazine/ETHOMEEN T12 ® or
ETHOMEEN S12 ®/TENOX Formulations at 40° C.
Nithiazine 0.0063 mole
Tenox 0.0007 mole

| Stabilizer | Initial | 30 days | 65 days |
|---|---|---|---|
| ETHOMEEN S12 ® (0.00011 mole) | 6.3803 | 5.8914 (92%) | 5.5140 (87%) |
| ETHOMEEN T12 ® (0.0017 mole) | 6.2924 | 5.8929 (94%) | 5.4528 (87%) |

Example 4

This example illustrates the UV stability for a number of nithiazine formulations containing both a stabilizer and an antioxidant. The UV stability tests were conducted as described above. Nithiazine was present initially in each formulation in an amount of 0.00623 mole. UV stability tests were used to determine appropriate amounts of amine and antioxidant in nithiazine product formulations.

| UV hour | % Nithiazine | wt % Nithiazine | UV hour | % Nithiazine | wt % Nithiazine |
|---|---|---|---|---|---|
| Tenox 0.00035 mole S12 ® 0.0008 mole | | | Tenox 0.0002 mole S12 ® 0.0003 mole | | |
| 0 | 100 | 5.5127 | 0 | 100 | 6.229 |
| 6 | 88.8 | 4.8927 | 6 | 89.3 | 5.560 |
| 22 | 69.8 | 3.848 | 22 | 75.8 | 4.7196 |
| 29 | 64.9 | 3.58 | 29 | 73.7 | 4.5803 |
| 46 | 53.3 | 2.9357 | 46 | 66 | 4.111 |
| Tenox 0.0007 mole S12 ® 0.0017 mole | | | Tenox 0.00063 mole S12 ® 0.001 mole | | |
| 0 | 100 | 5.7997 | 0 | 100 | 6.3803 |
| 6 | 91.1 | 5.2831 | 6 | 90.3 | 5.7629 |
| 24 | 73.6 | 4.2701 | 21 | 74 | 4.7236 |
| 31 | 72.4 | 4.1979 | 29 | 69.9 | 4.4627 |
| 47 | 64.2 | 3.7229 | 45 | 58.4 | 3.7254 |
| Tenox 0.0007 mole S12 ® 0.0022 mole | | | Tenox 0.00063 mole S12 ® 0.0017 mole | | |
| 0 | 100 | 6.1885 | 0 | 100 | 6.2924 |
| 6 | 90.3 | 5.5888 | 6 | 87.2 | 5.4861 |
| 24 | 73.8 | 4.5673 | 21 | 76.6 | 4.8224 |
| 31 | 70.7 | 4.3771 | 29 | 62.1 | 3.9082 |
| 47 | 65.9 | 4.0773 | 45 | 56.4 | 3.5518 |
| Tenox 0.0015 mole S12 ® 0.0078 mole | | | Tenox 0.0007 mole S12 ® 0.004 mole | | |
| 0 | 100 | 6.2586 | 0 | 100 | 5.7157 |
| 8 | 85.3 | 5.3198 | 7 | 75 | 4.2853 |
| 23 | 68 | 4.2532 | 23 | 39.2 | 2.2385 |
| 32 | 65.1 | 4.0740 | 31 | 29 | 1.6550 |
| 57 | 59.1 | 3.6957 | 47 | 22.8 | 1.3153 |
| Propyl gallate 0.0054 mole TEA 0.0059 mole | | | Tenox 0.00018 mole S12 ® 0.00014 mole | | |
| 0 | 100 | 6.491 | 0 | 100 | 6.0555 |
| 8 | 77.1 | 5.0061 | 6 | 89.2 | 5.401 |
| 23 | 57.5 | 3.7292 | 21 | 77 | 4.6596 |
| 32 | 52.3 | 3.3923 | 29 | 73.2 | 4.4312 |
| 57 | 39.6 | 2.5679 | 45 | 61.7 | 3.7373 |
| Tenox 0.00007 mole S12 ® 0.0008 mole | | | Tenox 0.00015 mole S12 ® 0.00043 mole | | |
| 0 | 100 | 5.5512 | 0 | 100 | 5.7912 |
| 7 | 80.5 | 4.4714 | 6 | 90 | 5.2117 |
| 23 | 60.3 | 3.3478 | 23 | 71.1 | 4.1161 |
| 31 | 54.7 | 3.0381 | 29 | 65.9 | 3.8137 |
| 47 | 48.7 | 2.7054 | 45 | 57 | 3.3005 |

Example 5

This example provides a comparison of the thermal stability of a nithiazine/Tenox/ETHOMEEN S12® formulation with a nithiazine/calcium hydroxide formulation. The nithiazine/Tenox/ETHOMEEN S12® formulation contained 0.006 mole of nithiazine, 0.001 mole Tenox and 0.002 mole ETHOMEEN S12®. The nithiazine/calcium hydroxide formulation contained an identical amount of nithizine, 0.002 mole calcium hydroxide and no antioxidant. The thermal stability of the formulation was evaluated at 40° C.

After 30 days, the calcium hydroxide formulation contained 75% of the nithiazine which was initially present; the Tenox/ETHOMEEN S12® formulation contained 91% of the nithiazine which was initially present At 51 days, the calcium hydroxide formulation contained 69% of the nithiazine which was initially present while the Tenox/ETHOMEEN S12® formulation contained 87% of the nithiazine which was initially present

TABLE 12

Thermal Stability of
Nithiazine/ETHOMEEN S12 ®/TENOX Formulation
Nithiazine 0.006 mole
Tenox 0.001 mole

| Stabilizer | Initial | 30 days | 51 days |
|---|---|---|---|
| ETHOMEEN S12 ® | 5.8385 | 5.2829 | 5.0669 |
| (0.0009 mole) | | (91%) | (87%) |
| Ca(OH)$_2$* | 5.4414 | 4.1037 | 3.7681 |
| (0.002 mole) | | (75%) | (69%) |

*contains no antioxidant Tenox GT-2

Example 6

This example provides a suitable formulation of nithiazine which contains both a thermal stabilizer and an antioxidant along with suitable carriers, surface agents and solvent.

| Ingredient | Amount |
|---|---|
| Ethanol | 25 mL |
| Nithiazine | 1 g (0.0062 mole) |
| ETHOMEEN S12 ® | 0.11 g (0.0003 mole) |
| TENOX GT-2 ® (70%) | 0.12 g (0.0002 mole) |
| Sodium propionate | 0.14 g |
| Carrageenan | 0.1 g |
| Polyethylene glycol #400 | 0.23 g |
| Sucrose | 13.62 g |
| PVP 120 | 0.42 g |
| Pigment yellow | 0.02 g |

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. An insecticidal composition comprising nithiazine and a hydroxyalkyl-tert-amine wherein said hydroxyalkyl-tert-amine and said nithiazine are present in a mole ratio of from about 0.01 to about 2.0.

2. A composition in accordance with claim 1, wherein said hydroxyalkyl-tert-amine is selected from the group consisting of N-Soyalkyl-2,2'-Iminobisethanol, N-Cocoalkyl-2,2'-Iminobisethanol and N-Tallowalkyl-2,2'-Iminobisethanol.

3. A composition in accordance with claim 1, wherein said hydroxyalkyl-tert-amine is a member selected from the group consisting of triethanolamine, 4(2-hydroxyethyl)morpholine, 4-(2-hydroxypropyl)morpholine, 4-(3-hydroxypropyl)morpholine, N-(2-hydroxyethyl)pyrrolidine, a lipophilic amine ethoxylate and a lipophilic amine propylate.

4. A composition in accordance with claim 1, wherein said hydroxyalkyl-tert-amine and said nithiazine are present in a mole ratio of from about 0.05 to about 0.5.

5. A composition in accordance with claim 1, wherein said hydroxyalkyl-tert-amine is a lipophilic amine ethoxylate, and said lipophilic amine ethoxylate and said nithiazine are present in a mole ratio of from about 0.05 to about 0.5.

6. A composition in accordance with claim 1, further comprising an antioxidant wherein said antioxidant and said hydroxyalkyl-tert-amine are present in a mole ratio of about 0.01 to about 2.0.

7. A composition in accordance with claim 6, wherein said antioxidant is a member selected from the group consisting of alkyl gallates, tocopherols, retinol, butylated hydroxytoluene, and butylated hydroxyanisol.

8. A composition in accordance with claim 6, wherein said antioxidant and said hydroxyalkyl-tert-amine are present in a mole ratio of about 1.0.

9. A composition according to claim 6, wherein said hydroxyalkyl-tert-amine is a lipophilic amine ethoxylate, said antioxidant is a mixture of tocopherols and said antioxidant and said hydroxyalkyl-tert-amine are present in a mole ratio of about 0.50 to about 2.0.

10. A method for controlling insects at a locus which comprises applying to said locus an insecticidally effective amount of a composition according to claim 1.

11. A method for controlling insects at a locus which comprises applying to said locus an insecticidally effective amount of a composition according to claim 5.

* * * * *